United States Patent [19]

Wu

[11] Patent Number: 4,912,281

[45] Date of Patent: Mar. 27, 1990

[54] CONVERSION OF METHANOL AND METHYL ETHER TO LIGHT OLEFINS WITH ZSM-45 IN PRESENCE OF HYDROGEN

[75] Inventor: Margaret M. Wu, Belle Meade, N.J.

[73] Assignee: Mobil Oil Corporation, New York, N.Y.

[21] Appl. No.: 296,405

[22] Filed: Jan. 9, 1989

Related U.S. Application Data

[63] Continuation of Ser. No. 566,372, Dec. 28, 1983, abandoned, which is a continuation-in-part of Ser. No. 449,910, Dec. 15, 1982, abandoned.

[51] Int. Cl.$^4$ ................................................. C07C 1/20
[52] U.S. Cl. .................................. 585/640; 585/639; 502/77; 502/53
[58] Field of Search ................... 585/640, 639; 502/53

[56] References Cited

U.S. PATENT DOCUMENTS

| | | | |
|---|---|---|---|
| 3,459,676 | 8/1969 | Kerr | 502/64 |
| 3,702,886 | 11/1972 | Argauer et al. | 502/64 |
| 3,709,979 | 1/1973 | Chu | 502/64 |
| 3,832,449 | 8/1974 | Rosinski | 208/111 |
| 4,066,714 | 1/1978 | Rodewald | 585/640 |
| 4,172,856 | 10/1979 | Spencer et al. | 585/640 |
| 4,358,395 | 11/1982 | Haeg et al. | 502/53 |
| 4,361,715 | 11/1982 | Shorl et al. | 585/640 |
| 4,423,272 | 12/1983 | Forbus et al. | 502/53 |
| 4,449,961 | 5/1984 | Forbus et al. | 585/640 |
| 4,495,303 | 6/1985 | Kuehl | 502/62 |
| 4,560,670 | 12/1985 | Pelrine | 502/53 |
| 4,683,052 | 7/1987 | Degnan, Jr. et al. | 502/63 |
| 4,777,156 | 10/1988 | Forbus et al. | 502/53 |

FOREIGN PATENT DOCUMENTS

| | | |
|---|---|---|
| 0001695 | 5/1979 | European Pat. Off. |
| 0040015 | 11/1981 | European Pat. Off. |

*Primary Examiner*—Asok Pal
*Attorney, Agent, or Firm*—A. J. McKillop; C. J. Speciale; E. F. Kenehan, Jr.

[57] ABSTRACT

A process is disclosed for converting a methanol and/or methyl ether-containing reactant feed along with a hydrogen-containing gaseous diluent to a light olefin-containing product over a ZSM-45 aluminosiloicate zeolite based catalyst composition. By using such ZSM-45 zeolite catalysts, methanol and/or methyl ether can be advantageously converted to an olefin-containing hydrocarbon product enriched in $C_2$ to $C_4$ olefins. The hydrogen-containing gaseous diluent is co-fed to the conversion reaction zone and the conversion reaction is conducted at a pressure of at least about 3 atmospheres in order to enhance catalyst lifetime.

16 Claims, No Drawings

CONVERSION OF METHANOL AND METHYL ETHER TO LIGHT OLEFINS WITH ZSM-45 IN PRESENCE OF HYDROGEN

CROSS-REFERENCE TO RELATED APPLICATION

This is a continuation of copending application Ser. No. 566,372, filed Dec. 28, 1983, now abandoned which is a continuation-in-part of applicants' copending U.S. application Ser. No. 449,910, filed Dec. 15, 1982, the entire disclosure of which is incorporated herein by reference, now abandoned.

BACKGROUND

This invention relates to an improved process for converting methanol and/or methyl ether to light olefins over crystalline aluminosilicate zeolite catalysts.

A remarkable growth in the production of synthetic fibers, plastics and rubber has taken place in recent decades. Such growth, to a large extent, has been supported and encouraged by an expanding supply of inexpensive petroleum raw materials such as ethylene and propylene. However, increasing demand for these light olefins has, from time to time, led to periods of shortage, either due to a diminished supply of suitable feedstocks or to limited processing capacity. In any event, it is now considered highly desirable to provide efficient means for converting raw materials other than petroleum to light olefins.

One such non-petroleum source of light olefins is coal-derived methanol and methyl ether. In this respect, it is known that methanol or methyl ether can be catalytically converted to olefin-containing hydrocarbon mixtures by contact under certain conditions with particular types of crystalline zeolite catalyst materials. U.S. Pat. No. 4,025,575, issued May 24, 1977, to Chang et al and U.S. Pat. No. 4,083,889, issued Apr. 11, 1978 to Caesar et al, for example, both disclose processes whereby methanol and/or methyl ether can be converted to an olefin-containing product over a ZSM-5 type (constraint index 1-12) zeolite catalyst. ZSM-5, in fact, converts methanol and/or methyl ether to hydrocarbons containing a relatively high concentration of light ($C_2$ and $C_3$) olefins with prolonged catalyst lifetime before catalyst regeneration becomes necessary.

It is also known that other types of zeolite catalysts can be used to convert methanol and/or methyl ether to olefin-containing hydrocarbon products containing even higher proportions of light olefins than can be realized by methanol/methyl ether conversion over ZSM-5. For example, U.S. Pat. Nos. 4,079,095 and 4,079,096, both issued Mar. 14, 1978, to Givens, Plank and Rosinski, disclose that zeolites of the erionite-offretite type, and especially ZSM-34, can usefully be employed to promote conversion of methanol and/or methyl ether to products comprising a major amount of $C_2$ and $C_3$ light olefins. However, while erionite-offretite type catalysts are highly selective to light olefins production, such smaller pore zeolites tend to age rapidly in comparison to ZSM-5 when used for methanol/methyl ether conversion.

U.S. Pat. No. 4,361,715 describes a process for making an olefin containing 6 or fewer carbon atoms in the molecule by reacting over a catalyst a feedstock comprising an oxygenated hydrocarbon and recovering the olefin from the products of the reaction. The catalyst for this process is said to comprise a zeolite designated as NU-3. This NU-3 zeolite is also described in U.S. Pat. No. 4,372,930.

The entire disclosures of the above-mentioned U.S. patents are expressly incorporated herein by reference.

In spite of the existence of methanol conversion processes utilizing a variety of zeolite catalysts, there is a continuing need to develop new procedures suitable for selectively converting an organic charge comprising methanol and/or methyl ether over zeolites catalysts to light olefin products with both high light olefin selectivity and prolonged catalyst lifetime.

Accordingly, it is an object of the present invention to provide a process for converting methanol and/or methyl ether over a zeolite-based catalyst to olefin-containing product with high selectivity to production of light olefins.

It is a further object of the present invention to provide such a selective process wherein lifetime of the zeolite catalyst is enhanced for methanol/methyl ether conversion.

It is a further object of the present invention to provide such a methanol/methyl ether conversion process employing a particular type of zeolite catalyst, readily available reactants and diluents and commercially practical reaction conditions.

SUMMARY

In accordance with an aspect of the present invention, a process is provided for the catalytic conversion of the organic reactants methanol and/or methyl ether to a hydrocarbon mixture containing light olefins. The catalyst employed in such a process comprises at least some synthetic porous crystalline material characterized as the aluminosilicate form of zeolite ZSM-45.

The aluminosilicate form of zeolite ZSM-45 is a high silica form of a levynite family of materials which exhibits a composition and properties distinguishing it from natural levynite. Zeolite ZSM-45 exhibits a characteristic X-ray powder diffraction pattern. Said X-ray diffraction pattern distinguishes it from other known synthetic and naturally occurring zeolites.

The porous crystalline zeolite ZSM-45, especially as calcined, is characterized by a distinctive X-ray diffraction pattern substantially as shown in Table 1 hereinafter. Zeolite ZSM-45 generally has a ratio of $XO_2 : Y_2O_3$ of at least 8, wherein X represents silicon and/or germanium and Y represents aluminum, boron, chromium, iron and/or gallium. Preferably, there are from greater than 8 to about 100 moles of $XO_2$ per mole of $Y_2O_3$. Preferably, $XO_2$ is silica and $Y_2O_3$ is alumina.

Zeolite ZSM-45 may have a composition, on an anhydrous basis and in terms of moles of oxides per mole of $Y_2O_3$, expressed by the formula:

$$(1-2.6)M_{2/m}O : Y_2O_3 : xXO_2 \qquad (I)$$

wherein M represents one or more cations having valence m and x is at least 8. In the above formula (I), M can be a hydrogen cation, provided that said hydrogen cation is bound to an anionic site on tetrahedra of said zeolite containing Y atoms. Of course, if M represented hydrogen not bound to said anionic sites, $M_{2/m}O$ would represent $H_2O$ which is impossible, because formula I is expressed on an anhydrous basis.

The as synthesized form of ZSM-45 may have a composition, on an anhydrous basis and in terms of moles of oxides per mole of alumina, expressed by the formula:

$(0.5–1.8)R_2O: (0.0–0.3)Na_2O: (0.0–0.5)K_2: Y_2O_3: xXO_2$ wherein $R_2O$ is the oxide form of a suitable directing agent and x is as defined hereinbefore. Particularly when R is derived from a 2-(hydroxyalkyl) trialkylammonium compound, there are, preferably, at least 0.8 moles of $R_2O$ per mole of $Y_2O_3$ in the as synthesized form of ZSM-45.

The term directing agent, as used herein, shall connote organic or organometallic compounds which are added to the crystallization mixture used to form a zeolite in order to influence the morphology of the ultimately formed crystal lattice. At least a portion of the cations corresponding to the directing agent are bound to anionic sites of the crystal lattice in the as synthesized form of the zeolite. Directing agents which have been verified as capable of influencing the formation of ZSM-45, provided that other ZSM-45 formation conditions are met, include 2-(hydroxyalkyl)trialkylammonium compounds, dimethyldiethylammonium compounds and cobalticinium compounds.

Methanol/methyl ether conversion over such a ZSM-45-containing catalyst occurs under conversion conditions which are sufficient to produce a light olefin containing product enriched in $C_2$–$C_4$ olefins, particularly ethylene. In accordance with the present invention, such conversion conditions include a pressure of at least $3 \times 10^5 N/m^2$. A gaseous diluent comprising a hydrogen-containing gas, e.g., hydrogen, is employed to prolong the lifetime of the zeolite catalyst in such a process.

DETAILED DESCRIPTION

In accordance with an aspect of the present invention, a ethanol and/or methyl ether containing organic reactant feed is catalytically converted to an olefin containing hydrocarbon product. The term "organic reactant feed" as used herein can comprise both the organic material used as reactants, i.e. the organic compounds such as methanol and methyl ether subjected to catalytic conversion to olefins, as well as additional components such as water or other diluents. Since methanol is miscible with water, the charge to the catalytic reaction zone may actually contain relatively large amounts of water, but only the methanol, methyl ether and associated organic compounds, constitute the reactant portion of the organic reactant feed.

Any methanol product comprising at least 60 wt. % of methanol may be used to provide methanol for the organic reactant feed in this invention. Substantially pure methanol, such as industrial grade anhydrous methanol, is eminently suitable. Crude methanol, which usually contains from 12 to 20 wt. % water, or more dilute solutions, also may be used.

Small amounts of impurities such as higher alcohols, aldehydes, or other oxygenated compounds in the organic reactant feed have little effect on the conversion reaction of this invention. The organic reactant feed may also comprise methyl ether. When this component is present, it can comprise up to 100% of the organic reactant feed or methyl ether can be admixed with methanol and/or water to form the organic reactant feed. For purposes of the present invention, it is contemplated to directly convert methanol and/or methyl ether in the feed to a hydrocarbon mixture characterized by a high content of light olefins, especially ethylene. Such amounts of methyl ether as may be formed concomitantly in the conversion reaction, however, may be recovered and recycled with fresh organic reactant feed.

In an embodiment of the present process, selectivity of the methanol conversion reaction for production of light ($C_2$–$C_3$) olefins can be increased by contacting methanol and/or methyl ether-containing feed with the hereinafter described zeolite based catalyst in the presence of up to about 20 mols, and preferably from about 1 to 10 mols of steam per mol of organic reactant. Such steam contact is made in the reaction zone under the methanol/methyl ether conversion conditions hereinafter described. Such steam may be provided directly by injecting the requisite amount of water or steam into the reaction zone. Alternatively, steam may be provided totally or in part by water present in the organic reactant feed in a molar ratio of water to organic reactants of up to about 20:1, preferably from about 1:1 to 10:1. Such water in the charge to the reaction zone, of course, forms steam in the reaction zone under the conversion conditions of the present invention. Steam can thus be passed to the reaction zone with a WHSV of from about 1 to 20, more preferably of from about 2 to 10.

The feedstock as hereinbefore described is catalytically converted to a product comprising light olefin-containing hydrocarbon product by contact with a catalyst composition comprising the aluminosilicate form of a particular type of synthetic porous crystalline zeolite material designated ZSM-45. Although zeolites were originally most commonly defined as materials containing silica and alumina, it is recognized that the silica and alumina portions may be replaced in whole or in part with other oxides. More particularly, $GeO_2$ is an art recognized substitute for $SiO_2$ and $B_2O_3$, $Cr_2O_3$, $Fe_2O_3$, and $Ga_2O_3$ are art recognized replacements for $Al_2O_3$. Accordingly, the term zeolite as used herein shall connote not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

The original alkali metal cations of the a synthesized ZSM-45 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the ZSM-45 catalytically active, especially for hydrocarbon conversion. These include hydrogen, rare earth metals and metals of Groups IA, IIA, IIIA, IVA, IB, IIB, IIIB, IVB and VIII of the Periodic Table of the Elements.

A typical ion exchange technique would be to contact the synthetic ZSM-45 with a salt of the desired replacing cation or cations. Examples of such salts include the halides, e.g. chlorides, nitrates and sulfates.

Catalytically active zeolite ZSM-45 described and claimed herein has a definite X-ray diffraction pattern which distinguishes it from other crystalline materials. The X-ray diffraction pattern of zeolite ZSM-45, especially as calcined, has the following characteristic lines:

TABLE 1

| Interplanar D-Spacing (A) | Relative Intensity, I/Io |
|---|---|
| 11.34 ± 0.20 | Weak |
| 10.16 ± 0.18 | Weak |
| 8.02 ± 0.14 | Strong–Very Strong |
| 7.56 ± 0.14 | Weak |
| 6.55 ± 0.12 | Medium–Very Strong |
| 5.66 ± 0.10 | Weak |
| 5.50 ± 0.10 | Weak |
| 5.07 ± 0.09 | Medium–Strong |
| 4.95 ± 0.09 | Weak |
| 4.21 ± 0.08 | Medium–Strong |
| 4.01 ± 0.07 | Strong–Very Strong |
| 3.78 ± 0.07 | Medium–Strong |
| 3.60 ± 0.06 | Weak |
| 3.54 ± 0.06 | Weak–Medium |
| 3.42 ± 0.06 | Weak |
| 3.27 ± 0.06 | Medium |
| 3.11 ± 0.06 | Medium–Strong |
| 3.03 ± 0.05 | Weak |
| 2.812 ± 0.05 | Weak |
| 2.751 ± 0.05 | Medium–Strong |
| 2.583 ± 0.05 | Weak |
| 2.535 ± 0.05 | Weak |
| 2.521 ± 0.05 | Weak |
| 2.475 ± 0.04 | Weak |
| 2.405 ± 0.04 | Weak |
| 2.362 ± 0.04 | Weak |
| 2.251 ± 0.04 | Weak |
| 2.181 ± 0.04 | Weak |
| 2.133 ± 0.04 | Weak |
| 2.097 ± 0.04 | Weak |
| 2.029 ± 0.04 | Weak |
| 2.006 ± 0.03 | Weak |
| 1.889 ± 0.03 | Weak |
| 1.859 ± 0.03 | Weak |
| 1.843 ± 0.03 | Weak |
| 1.815 ± 0.03 | Weak |
| 1.765 ± 0.03 | Weak |
| 1.721 ± 0.03 | Weak |
| 1.710 ± 0.03 | Weak |
| 1.650 ± 0.03 | Weak |
| 1.637 ± 0.03 | Weak |
| 1.617 ± 0.03 | Weak |
| 1.606 ± 0.03 | Weak |
| 1.559 ± 0.03 | Weak |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Angstrom units (A), corresponding to the recorded lines, were determined. In Table 1, the relative intensities are given in terms of the strongest line being taken as 100.0. It should be understood that this X-ray diffraction pattern is characteristic of all the species of zeolite ZSM-45 compositions. The sodium form as well as other cationic forms reveal substantially the same pattern with some minor shifts in interplanar spacing and variation in relative intensity. Other minor variations can occur, depending on the silicon to aluminum ratio of the particular sample, as well as its degree of thermal treatment.

Zeolite ZSM-45 sorbs significant amounts of commonly used test adsorbent materials, i.e. cyclohexane, n-hexane and water, whereas naturally occurring levynite is not expected to adsorb cyclohexane due to its pore structure. Sorption capacities for zeolite ZSM-45 may range at room temperature as follows:

| Adsorbate | Capacity, Wt. Percent |
|---|---|
| Cyclohexane | 2–5 |
| n-Hexane | 7–15 |
| Water | 14–25 | wherein cyclohexane and n-hexane sorption are measured at 20 Torr and water sorption is measured at 12 Torr.

The zeolite of the present invention can be used either in the alkali metal form, e.g. the sodium or potassium form; the ammonium form; the hydrogen form or another univalent or multivalent cationic form. When used as a catalyst the zeolite will be subjected to thermal treatment to remove part or all of the organic constituent.

The zeolite can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition to the extent atom Y, e.g., aluminum, is in the structure, impregnated therein or intimately physically admixed therewith. Such component can be impregnated in or on to it such as for example, by, in the case of platinum, treating the zeolite with a solution containing a platinum metal-containing ion. Thus, suitable platinum compounds include chloroplatinic acid, platinous chloride and various compounds containing the platinum amine complex.

Zeolite ZSM-45, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the catalysis of certain hydrocarbon conversion reactions.

The new zeolite, when employed either as an adsorbent or as a catalyst in an organic compound conversion process should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing ZSM-45 in a vacuum, but a longer time is required to obtain a sufficient amount of dehydration.

The new zeolite can be prepared from a reaction mixture containing sources of alkali metal ions (Z), an oxide of Y, an oxide of X, an organic or organometallic cation (R), and water. When R is derived from a 2-(hydroxyalkyl)trialkylammonium compound wherein alkyl is composed of one or two carbon atoms, the reaction mixture may comprise an appropriate ZSM-45 formation selection of reactants, having a composition, in terms of mole ratios of oxides, falling within the following ranges:

| Reactants | Useful | Preferred |
|---|---|---|
| $SiO_2/Al_2O_3$ | 10–150 | 15–80 |
| $OH^-/SiO_2$ | 0.3–1.0 | 0.3–0.8 |
| $H_2O/OH^-$ | 20–100 | 20–80 |
| R/(R + Z) | 0.1–0.8 | 0.2–0.7 |
| K/(K + Na) | 0.0–0.8 | 0.05–0.3 | wherein R and Z are as above defined.

When R is a dimethyldiethylammonium (DMDEA) compound, the reaction mixture may, optionally, be essentially free of potassium ions and may comprise an appropriate ZSM-45 formation selection of reactants, in terms of mole ratios of oxides, falling within the following ranges:

| Reactants | Useful | Preferred |
|---|---|---|
| $SiO_2Al_2O_3$ | 10–80 | 20–60 |
| $H_2O/OH^-$ | 15–100 | 20–80 |
| $OH^-/SiO_2$ | 0.40–0.80 | 0.50–0.70 |
| DMDEA/(DMDEA + Z) | 0.75–1.0 | 0.8–0.95 | wherein Z is as above defined.

When R is a cobalticinium compound, the reaction mixture may comprise an appropriate ZSM-45 formation selection of reactants, in terms of mole ratios of oxides, falling within the following ranges:

| Reactants | Useful | Preferred |
|---|---|---|
| $SiO_2/Al_2O_3$ | 10–30 | 10–15 |
| $OH^-/SiO_2$ | 0.005–1.0 | 0.2–0.6 |
| $Z/SiO_2$ | 0.001–5.0 | 0.1–1.5 |
| $H_2O/SiO_2$ | 10–200 | 20–100 |
| $R/SiO_2$ | 0.01–3 | 0.05–1.5 | wherein R and Z are as above defined.

Crystallization of the new zeolite ZSM-45 can be carried out at either static or stirred conditions in a suitable reactor vessel, such as for example, polypropylene jars or teflon lined or stainless steel autoclaves. A useful range of temperatures for crystallization is from about 80° C. to about 350° C. for a time of about 12 hours to about 200 days. Thereafter, the crystals are separated from the liquid and recovered. The composition can be prepared utilizing materials which supply the appropriate oxides. Such compositions may include sodium silicate, silica hydrosol, silica gel, silicic acid, sodium hydroxide, a source of aluminum, and an appropriate organic compound. It should be realized that the reaction mixture component oxides can be supplied from more than one source. The reaction mixture can be prepared either batchwise or continuously. Crystal size and crystallization time of the new crystalline zeolite ZSM-45 will vary with the nature of the reaction mixture employed and the crystallization conditions.

In all cases, synthesis of the ZSM-45 crystals is facilitated by the presence of at least 0.01 percent, preferably 0.10 percent and still more preferably 1 percent, seed crystals (based on total weight) of crystalline product.

It will be readily understood by those of ordinary skill in the art that the above recitation of useful and preferred ranges of reactants does not constitute a warranty that all possible combinations of reactants falling within these ranges will automatically lead to the production of ZSM-45. To the contrary, for example, the Rubin et al U.S. Pat. No. 4,086,186, the entire disclosure of which is expressly incorporated herein by reference, describes the formation of ZSM-34 with a chlorine chloride directing agent and reactants falling within the above-recited ranges for the use of such a directing agent. Accordingly, one must select reactants and crystallization conditions in a manner sufficient to lead to the formation of ZSM-45. This selection will be readily enabled by the guidance provided herein, especially with regard to the Examples and Comparative Examples recited hereinafter. In this regard, it is particularly noted that, when choline chloride is used as a directing agent, sufficiently high concentrations of potassium ions in the reaction mixture would appear to lead to the formation of ZSM-34 instead of ZSM-45. Accordingly, if, in a first attempt to make ZSM-45 using a choline chloride directing agent, one inadvertently made ZSM-34 instead, the second attempt might involve, e.g., lowering of the potassium ion concentration. Similarly, unsuccessful first attempts in the course of routine experimentation, which depart from the express reactant selections and conditions of the Examples recited hereinafter, could be followed by second attempts more closely corresponding with the express reactant selections and conditions of the Examples recited hereinafter.

It is further noted that the use of an appropriate seed crystal could theoretically change an otherwise non-ZSM-45 forming reactant mixture (e.g., a mixture capable of forming ZSM-34) to a mixture capable of forming ZSM-45.

When a 2-(hydroxyalkyl)trialkylammonium directing agent is used, the 2-(hydroxyalkyl)trialkylammonium compound may be the hydroxide or halide, e.g. chloride, iodide or bromide. When the compound is 2-(hydroxyethyl)trimethylammonium chloride, it is called choline chloride, a preferred source of organic cations (R) in the synthesis of zeolite ZSM-45.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In the case of many catalysts, it is desired to incorporate the new zeolite ZSM-45 with another material resistant to the temperatures and other conditions employed in organic conversion processes. Such materials include active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the new ZSM-45 crystal, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the xontmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the zeolite ZSM-45 can be composited with a porous matrix material such as silica-alumina, silica-magnesia, silica-zirconia, silica-thoria, silica-beryllia, silica-titania as well as ternary compositions such as silica-alumina-thoria, silica alumina-zirconia, silica alumina-magnesia and silica-magnesia-zirconia. The relative proportions of finely divided crystalline material and inorganic oxide gel matrix vary widely, with the zeolite content ranging from about 1 to about 90 percent by weight and more usually, particularly when the composite is prepared in the form of beads, in the range of about 2 to about 80 weight percent of the composite.

As noted, the ZSM-45 zeolite containing catalyst compositions as hereinbefore described are especially useful for the selective conversion of methanol and/or methyl ether to a light olefin ($C_2$-$C_4$)-containing hydrocarbon product particularly enriched in ethylene By utilizing a selected combination of the particular ZSM-45 based catalyst along with particular methanol/methyl ether conversion reaction conditions, methanol/methyl ether conversion processes as can be realized which are more selective to light olefin production than are similar processes employing other types of zeolite catalysts. Processes utilizing these particular ZSM-45 based catalysts and certain reaction conditions are also more resistant to catalyst aging or provide enhanced conversion of methanol and/or methyl ether-containing feed to olefins in comparison with other known zeolite-catalyzed methanol/methyl ether conversion processes. The process of the present invention, in fact, yields a light olefin-containing product wherein ethylene is the major light olefin produced.

In accordance with the present process invention, a chargestock comprising methanol (methyl alcohol), methyl ether, methanol/methyl ether mixtures or mixtures of such organic materials along with a gaseous diluent comprising a hydrogen-containing gas can be contacted in the vapor phase with the ZSM-45-based catalyst materials hereinbefore described in a reaction zone and under reaction conditions suitable for effecting conversion of methanol and/or methyl ether to olefins. Such conditions include an operating temperature between about 260° C. ($\sim$500° F.) and 540° C. ($\sim$1000° F.), preferably 300° C. and 450° C.; a pressure of at least about $3 \times 10^5$ N/m² (3 atmospheres), preferably from about $3 \times 10^5$ N/m² to about $1.5 \times 10^6$ N/m² (15 atmospheres); and a weight hourly space velocity (WHSV) of the organic reactants between about 0.1 and 30, preferably 0.1 and 10.

In addition to hydrogen, further carrier gases or diluents may also be injected into the reaction zone such as, for example, nitrogen, helium, water, carbon monoxide, carbon dioxide, or mixtures of these gases. A hydrogen-containing gaseous diluent provides a reducing atmosphere in the methanol conversion reaction zone. Such a hydrogen-containing gas can be selected from substantially pure hydrogen and mixtures of hydrogen and carbon monoxide such as are found in synthesis gas.

Whatever the nature of the particular hydrogen-containing gaseous diluent utilized, it has been found that hydrogen-containing gaseous diluents of the type described herein can usefully be employed to prolong the lifetime and selectivity of the ZSM-45 zeolite based methanol/methyl ether conversion catalyst when such catalysts and diluents are employed under particular conditions for the selective conversion of methanol/methyl ether to light olefins. The gaseous diluent can be co-fed using a weight hourly space velocity (WHSV) of from about 0.003 to 20, preferably from about 0.01 to 10. Generally the molar ratio of gaseous diluent to the organic reactants ranges from about 0.05:1 to 40:1, more preferably from about 0.1:1 to 20:1.

Conversion reaction conditions, including the presence or absence of diluents, can affect the selectivity of the present methanol/methyl ether conversion process to light olefin and ethylene production as well as percent conversion of organic reactants to hydrocarbon product and catalyst aging characteristics. However, it has been discovered that for a given set of reaction conditions the ZSM-45 based catalyst used in the present invention used in combination with a hydrogen-containing gaseous diluent, will generally provide improved methanol conversion light olefin selectivity and/or catalyst aging performance in comparison with similar prior art processes employing other zeolites or zeolite-diluent combinations.

It should be noted that "catalyst lifetime" as used herein refers to the length of time on stream during which a catalyst can be employed before catalytic activity drops to a level such that catalyst regeneration becomes commercially desirable or necessary. A convenient measurement of catalyst lifetime would be the length of time a catalyst can be employed in the process of the present invention before methanol/methyl ether conversion in the process drops from its initial value to an arbitrarily set lower conversion value, e.g., 50% conversion. For purposes of the present invention, enhanced catalyst lifetime refers to the extension of the catalyst lifetime which can be realized with a process using the ZSM-45/hydrogen-containing gaseous diluent combination in comparison with prior art methanol/methyl ether conversion processes wherein this particular zeolite/diluent combination is not employed.

The methanol and/or methyl ether conversion process described herein may be carried out as a batch-type, semi-continuous or continuous operation utilizing a fixed, fluidized or moving bed catalyst system. A preferred embodiment entails use of a catalyst zone wherein the alcohol or ether charge optionally together with added water is passed concurrently or countercurrently through a fluidized or moving bed of particleform catalyst. The latter after use may be conducted to a regeneration zone wherein catalyst can be regenerated by any of the conventional regeneration methods known to the art and thereafter recycled to the conversion zone for further contact with the methanol and/or ether containing feed.

The product stream in the process of the invention contains steam and a hydrocarbon mixture of paraffins and olefins, which mixture can be substantially devoid of aromatics. As noted, the mixture is particularly rich in light olefins, and especially rich in ethylene. Thus, the predominant hydrocarbon product constitutes valuable petrochemicals. The steam and hydrocarbon products may be separated from one another by methods well known in the art. In a preferred embodiment of the invention, the unconverted methanol and/or methyl ether, as well as at least part of the water in the product, can be recycled to the reaction zone.

In order to more fully illustrate the nature of the invention and the manner of practicing same, the following examples are presented. In the examples, whenever adsorption data are set forth for comparison of sorptive capacities of ZSM-45 for water, cyclohexane and/or n-hexane, they were determined as follows:

A weighed sample of the calcined ZSM-45 adsorbent was contacted with the desired pure adsorbate vapor in an adsorption chamber, evacuated to less than 1 mm and contacted with 12 mm Hg of water vapor or 20 mm Hg of n-hexane, or cyclohexane vapor, pressures less than the vapor-liquid equilibrium pressure of the respective adsorbate at room temperature. The pressure was kept constant (within about ±0.5 mm) by addition of adsorbate vapor controlled by a manostat during the adsorption period, which did not exceed about 8 hours. As adsorbate was adsorbed by the zeolite crystal, the decrease in pressure caused the manostat to open a valve which admitted more adsorbate vapor to the chamber to restore the above control pressures. Sorption was complete when the pressure change was not sufficient to activate the xanostat. The increase in weight was calculated as the adsorption capacity of the sample in g/100 g of calcined adsorbent.

When Alpha Value for the ZSM-45 zeolite is examined, it is noted that the Alpha Value is an approximate indication of the catalytic activity, e.g., cracking activity, of the catalyst compared to a standard catalyst and it gives the relative rate constant (rate of normal hexane conversion per volume of catalyst per unit time). It is based on the activity of the highly active silica-alumina cracking catalyst taken as an Alpha Value of 1 (Rate Constant $=0.016$ sec$^{-1}$). The Alpha Test is described in U.S. Pat. No. 3,354,078 and in The Journal of Catalysis, Vol. IV, pp. 522-529 (Aug. 1965), both incorporated herein by reference as to that description.

EXAMPLE 1

Three separate components were prepared to comprise ingredients as follows:

| | | |
|---|---|---|
| A. | 15.45 | grams of $Al_2(SO_4)_3 \cdot 18H_2O$ |
| | 3.48 | grams of $H_2SO_4$ |
| | 90.2 | grams of $H_2O$ |
| B. | 135.4 | grams of Q-Brand sodium silicate (28.5 wt. percent $SiO_2$, 8.8 wt. percent $Na_2O$ and 62.7 wt. percent $H_2O$) |
| | 2.0 | grams of 86.4 wt. percent KOH |
| | 11.0 | grams of $H_2O$ |
| C. | 38.0 | grams of choline chloride |

Component C was added to component B and A was then added to the whole. The whole composition was then mixed and the mixture was transferred to a polypropylene jar. Crystallization occurred under static conditions at 99° C. over 197 days. The crystalline product was separated, washed and dried and identified by X-ray diffraction analysis to be about 90 percent Zeolite ZSM-45 plus about 10 percent unidentified impurities. The complete X-ray pattern data for this zeolite is presented in Table 2, hereinafter.

Chemical analysis of the zeolite product of this example proved it to have the following composition:

| Component | Wt. Percent |
|---|---|
| N | 2.07 |
| Na | 0.28 |
| K | 0.35 |
| $Al_2O_3$ | 7.40 |
| $SiO_2$ | 89.90 |
| Ash | 80.50 |
| $SiO_2/Al_2O_3$, molar | 20.7 |

Sorption capacities of the zeolite product of this example, calcined at 538° C., were:

| Adsorbate | Capacity, Wt. Percent |
|---|---|
| Cyclohexane, 20 Torr | 3.5 |
| n-Hexane, 20 Torr | 12.9 |
| Water, 12 Torr | 18.3 |

The surface area of the Zeolite ZSM-45 product of this example was measured to be 514 m$^2$/gram.

TABLE 2

| Degrees Two Theta | Interplanar D-Spacing (A) | Relative Intensity, I/Io |
|---|---|---|
| 7.72 | 11.45 | 6 |
| 8.60 | 10.28 | 13 |
| 10.91 | 8.11 | 50 |
| 11.45 | 7.73 | 3 |
| 11.65 | 7.60 | 6 |
| 13.41 | 6.60 | 36 |
| 15.60 | 5.68 | 6 |
| 16.00 | 5.54 | 9 |
| 17.38 | 5.10 | 81 |
| 17.84 | 4.97 | 12 |
| 20.98 | 4.23 | 51 |
| 22.08 | 4.03 | 100 |
| 23.44 | 3.80 | 45 |
| 25.05 | 3.55 | 13 |
| 25.53 | 3.49 | 5 |
| 25.94 | 3.43 | 5 |
| 27.12 | 3.29 | 20 |
| 28.53 | 3.13 | 47 |
| 29.38 | 3.04 | 6 |
| 31.70 | 2.823 | 8 |
| 32.45 | 2.759 | 40 |
| 34.57 | 2.595 | 10 |
| 35.25 | 2.546 | 2 |
| 35.46 | 2.531 | 2 |
| 38.08 | 2.363 | 2 |
| 38.41 | 2.344 | 1 |
| 39.80 | 2.265 | 3 |
| 40.50 | 2.227 | 1 |
| 41.25 | 2.189 | 3 |
| 42.23 | 2.140 | 3 |
| 43.00 | 2.103 | 8 |
| 44.52 | 2.035 | 2 |
| 45.10 | 2.010 | 4 |
| 46.89 | 1.938 | 1 |
| 47.32 | 1.921 | 1 |
| 48.02 | 1.895 | 6 |
| 48.90 | 1.863 | 6 |
| 49.40 | 1.845 | 3 |
| 50.10 | 1.821 | 7 |
| 51.61 | 1.771 | 12 |
| 52.42 | 1.745 | 1 |
| 53.00 | 1.728 | 2 |
| 53.50 | 1.713 | 1 |
| 54.10 | 1.695 | 1 |
| 55.00 | 1.670 | 1 |
| 55.58 | 1.653 | 3 |

TABLE 2-continued

| Degrees Two Theta | Interplanar D-Spacing (A) | Relative Intensity, I/Io |
|---|---|---|
| 56.02 | 1.642 | 8 |
| 56.82 | 1.620 | 3 |
| 57.35 | 1.607 | 2 |
| 59.15 | 1.562 | 5 |

COMPARATIVE EXAMPLE A

This Comparative Example demonstrates that ZSM-45 will not form unless sufficient ZSM-45 forming conditions are maintained. More particularly, this Comparative Example corresponds to Example 8 of the Rubin et al U.S. Pat. No. 4,086,186, wherein ZSM-34 was synthesized from mixtures containing aluminum sulfate and sodium silicate. Utilizing these reactants, a solution containing 15.98 grams of $Al_2(SO_4)_3 \cdot 18 H_2O$ in 100 grams of water was added to a solution of 135.4 grams of Q-Brand sodium silicate (8.8 percent $SiO_2$, 8.9 percent $Na_2O$ and 62 percent $H_2O$) and 40 grams of 4.4 grams of KOH (86.4 percent) and 38 grams of choline chloride had been added. A gel formed having the following molar composition:

$$\frac{SiO_2}{Al_2O_3} = 27.2$$

$$\frac{R^+}{R^+ + Z^+} = 0.46$$

$$\frac{OH^-}{SiO_2} = 0.48$$

$$\frac{H_2O}{OH^-} = 39.6$$

$$\frac{K_2O}{Z_2O} = 0.22$$

This material was permitted to crystallize in a propylene container by exposure to a temperature of 210° F. for 98 days. The crystalline product obtained was filtered, water washed and dried at 230° F. and upon analysis was found to be ZSM-34 having the following molar composition:

0.93 $R_2O$: 0.22 $K_2O$: 0.08 $Na_2O$: $Al_2O_3$: 13.7 $SiO_2$

The product obtained, after calcination at 1000° F. for 16 hours, had the following sorptive and surface area properties:

| Sorption | Wt. Percent |
|---|---|
| Cyclohexane | 3.1 |
| n-Hexane | 10.5 |
| Water | 19.0 |
| Surface Area $M^2/g$ | 528 |

Noted distinctions between Example 1 and Comparative Example A are (i) that the ratio of $K^+$ to $SiO_2$ in the reaction mixture of parative Example A is more than twice that of Example 1, and (ii) that the potassium to aluminum ratio in the reaction mixture of parative Example A exceeds one, whereas the potassium to aluminum ratio in the reaction mixture of Example 1 is less than one.

EXAMPLE 2

About 10 grams of the Zeolite ZSM-45 product of Example 1 was calcined in air at 538° C. for 10 hours and then contacted with 10 cc/gram zeolite of 5 percent ammonium chloride solution at 29° C. five separate times. The resulting zeolite was then dried at about 110° C. and calcined at 538° C. for 10 hours in air. It was then submitted for evaluation in the Alpha Test. Its Alpha Value proved to be 14.

EXAMPLE 3

Three separate components were prepared to comprise ingredients as follows:

| | |
|---|---|
| A. | 15.45 grams of $Al_2(SO_4)_3 \cdot 18H_2O$ |
| | 3.48 grams of $H_2SO_4$ |
| | 90.2 grams of $H_2O$ |
| B. | 135.4 grams of Q-Brand sodium silicate (28.5 wt. percent $SiO_2$, 8.8 wt. percent $Na_2O$ and 62.7 wt. percent $H_2O$) |
| | 2.0 grams of 86.4 wt. percent KOH |
| | 50.0 grams of $H_2O$ |
| C. | 38.0 grams of choline chloride |

Component C was added to component B and component A was then added to the whole. The whole composition was then mixed and the mixture was transferred to a polypropylene jar. Crystallization occurred under static conditions at 99° C. over 152 days. The crystalline product was separated, washed and dried and identified by X-ray diffraction analysis to be the new zeolite ZSM-45.

Chemical analysis of the zeolite product of this example proved it to have the following composition:

| Component | Wt. Percent |
|---|---|
| N | 2.25 |
| Na | 0.43 |
| K | 0.25 |
| $Al_2O_3$ | 7.60 |
| $SiO_2$ | 89.00 |
| Ash | 78.90 |

Sorption capacities of the zeolite product of this example, calcined at 538° C., were:

| Adsorbate | Capacity, Wt. Percent |
|---|---|
| Cyclohexane, 20 Torr | 3.8 |
| n-Hexane, 20 Torr | 11.3 |
| Water, 12 Torr | 16.2 |

The surface area of the zeolite product of this example was measured to be 467 $m^2$/gram.

EXAMPLE 4

About 10 grams of the zeolite ZSM-45 product of Example 3 was calcined in air at 538° C. for 10 hours and then contacted with 5 percent ammonium chloride solution, dried and calcined as in Example 2. It was then submitted for evaluation in the Alpha Test. Its Alpha Value proved to be 6.

EXAMPLE 5

Three separate components were prepared to comprise ingredients as follows:

| | |
|---|---|
| A. | 28.7 grams of sodium aluminate |
| | 36.0 grams of NaOH |
| | 10.0 grams of 85 wt. percent KOH |
| | 450.0 grams of H₂O |
| B. | 650.0 grams of colloidal silica (30 wt. percent) |
| C. | 190.0 grams of choline chloride |

C. 190.0 grams of choline chloride

Component C was added to component A and component B was then added to the whole. The whole composition was then mixed and the mixture was transferred to a polypropylene jar. Crystallization occurred under static conditions at 121° C. over 21 days. The crystalline product was separated, washed and dried and identified by X-ray diffraction analysis to be about 85 percent new zeolite ZSM-45 plus about 15 percent unidentified impurities. The complete X-ray pattern data for this zeolite is presented in Table 3, hereinafter.

Chemical analysis of the zeolite product of this example proved it to have the following composition:

| Component | Wt. Percent |
|---|---|
| N | 2.34 |
| Na | 0.49 |
| K | 0.58 |
| $Al_2O_3$ | 6.90 |
| $SiO_2$ | 72.60 |
| Ash | 81.50 |

Sorption capacities of the zeolite product of this example, calcined at 538° C., were:

| Adsorbate | Capacity, Wt. Percent |
|---|---|
| Cyclohexane, 20 Torr | 5.0 |
| n-Hexane, 20 Torr | 11.0 |
| Water, 12 Torr | 14.5 |

The surface area of the zeolite product of this example was measured to be 484 m²/gram.

TABLE 3

| Degrees Two Theta | Interplanar D-Spacing (A) | Relative Intensity, I/Io |
|---|---|---|
| 7.78 | 11.36 | 14 |
| 8.67 | 10.20 | 11 |
| 11.00 | 8.04 | 37 |
| 11.69 | 7.57 | 8 |
| 12.60 | 7.03 | 4 |
| 13.15 | 6.73 | 8 |
| 13.49 | 6.60 | 37 |
| 15.55 | 5.70 | 6 |
| 16.05 | 5.52 | 9 |
| 17.45 | 5.08 | 65 |
| 17.88 | 4.96 | 20 |
| 19.45 | 4.56 | 6 |
| 20.72 | 4.29 | 20 |
| 21.07 | 4.22 | 47 |
| 22.12 | 4.02 | 100 |
| 23.49 | 3.79 | 62 |
| 25.14 | 3.54 | 38 |
| 25.91 | 3.44 | 18 |
| 26.90 | 3.31 | 10 |
| 27.19 | 3.28 | 27 |
| 28.35 | 3.15 | 13 |
| 28.63 | 3.12 | 40 |
| 29.40 | 3.04 | 7 |
| 31.54 | 2.84 | 11 |
| 31.75 | 2.819 | 10 |
| 32.51 | 2.754 | 35 |
| 34.65 | 2.589 | 6 |
| 35.50 | 2.529 | 2 |
| 36.25 | 2.478 | 5 |
| 38.10 | 2.362 | 3 |
| 39.80 | 2.265 | 2 |
| 41.25 | 2.189 | 2 |
| 42.28 | 2.138 | 3 |
| 43.05 | 2.101 | 7 |
| 45.17 | 2.007 | 3 |
| 48.11 | 1.891 | 5 |
| 48.90 | 1.863 | 4 |
| 49.45 | 1.843 | 3 |
| 50.19 | 1.817 | 6 |
| 51.74 | 1.767 | 11 |
| 52.94 | 1.730 | 1 |
| 55.68 | 1.651 | 4 |
| 56.15 | 1.638 | 6 |
| 56.94 | 1.617 | 1 |
| 59.26 | 1.559 | 3 |

EXAMPLE 6

About 10 grams of the zeolite ZSM-45 product of Example 5 was calcined in air at 538° C. for 10 hours and then contacted with 5 percent ammonium chloride solution, dried and calcined as in Example 4. It was then submitted for evaluation in the Alpha Test. Its Alpha Value proved to be 27.

COMPARATIVE EXAMPLE B

This Comparative Example again demonstrates that ZSM-45 will not form unless sufficient ZSM-45 forming conditions are maintained. More particularly, this Comparative Example corresponds to Example 1 of the Rubin et al U.S. Pat. No. 4,086,186, wherein ZSM-34 was synthesized from a reaction mixture containing 4.43 grams of KOH (86.4 percent), 13 grams of NaOH (96 percent) and 5.74 grams of sodium aluminate (43.1 percent $Al_2O_3$, 33.1 percent $Na_2O$, 24 percent $H_2O$) dissolved in 90 grams of water. Choline chloride (38 grams) was added to the resulting solution, followed by the addition of 130 grams of colloidal silica (30 Wt. percent $SiO_2$ and 70 Wt. percent $H_2O$). A gel formed having the following molar composition:

$$\frac{SiO_2}{Al_2O_3} = 26.6$$

$$\frac{R^+}{R^+ + Z^+} = 0.38$$

$$\frac{OH^-}{SiO_2} = 0.68$$

$$\frac{H_2O}{OH^-} = 22.9$$

$$\frac{K_2O}{Z_2O} = 0.15$$

where R is choline [$(CH_3)_3NCH_2CH_2OH$] and Z is Na+K.

The resulting gel was mixed for 15 minutes and allowed to crystallize in a polypropylene container at 210° F. for 25 days. The crystalline product obtained was separated from the mother liquor by filtration, water washed and dried at 230° F. This product, upon analysis, was found to have the following composition molar ratio:

0.64 R$_2$O: 0.47 K$_2$O: 0.13 Na$_2$O: Al$_2$O$_3$: 10.8 SiO$_2$ and the following X-ray diffraction pattern:

| Degrees Two Theta | Interplanar D-Spacing (A) | Relative Intensity, I/Io |
|---|---|---|
| 7.65 | 11.56 | 100 |
| 9.60 | 9.21 | 3 |
| 11.65 | 7.60 | 25 |
| 13.37 | 6.62 | 52 |
| 14.01 | 6.32 | 10 |
| 15.45 | 5.74 | 31 |
| 16.62 | 5.33 | 4 |
| 17.82 | 4.98 | 10 |
| 19.40 | 4.58 | 64 |
| 20.50 | 4.33 | 61 |
| 21.35 | 4.16 | 7 |
| 23.31 | 3.82 | 55 |
| 23.67 | 3.76 | 86 |
| 24.77 | 3.59 | 86 |
| 27.03 | 3.30 | 34 |
| 28.25 | 3.16 | 40 |
| 30.55 | 2.926 | 9 |
| 31.35 | 2.853 | 84 |
| 31.92 | 2.804 | 11 |
| 33.45 | 2.679 | 16 |
| 35.70 | 2.515 | 4 |
| 36.10 | 2.488 | 21 |
| 39.41 | 2.286 | 4 |
| 41.02 | 2.200 | 7 |
| 42.90 | 2.108 | 6 |
| 43.50 | 2.080 | 4 |
| 45.75 | 1.983 | 4 |
| 46.42 | 1.956 | 3 |
| 48.15 | 1.890 | 19 |
| 48.83 | 1.865 | 5 |
| 49.84 | 1.830 | 6 |

A portion of the product, calcined at 1000° F. for 16 hours, had the following sorption and surface area properties:

| Sorption | Wt. Percent |
|---|---|
| Cyclohexane | 4.4 |
| n-Hexane | 11.5 |
| Water | 22.2 |
| Surface Area M$^2$/g | 523 |

Noted distinctions between Example 5 and Comparative Example B are (i) that the ratio of K+ to SiO$_2$ in the reaction mixture of parative Example B is more than twice that of Example 5, and (ii) that the potassium to aluminum ratio in the reaction mixture of Comparative Example B exceeds one, whereas the potassium to aluminum ratio in the reaction mixture of Example 5 is less than one.

EXAMPLE 7

Three separate components were prepared to comprise ingredients as follows:

| | |
|---|---|
| A. | 23.2 grams of Al$_2$(SO$_4$)$_3$.18 H$_2$O |
| | 5.2 grams of H$_2$SO$_4$ |
| | 135 grams of H$_2$O |
| B. | 203.1 grams of Q-Brand sodium silicate (28.5 wt. percent SiO$_2$, 8.8 wt. percent Na$_2$O and 62.7 wt. percent H$_2$O) |
| | 3.0 grams of 86.4 wt. percent KOH |
| | 75.0 grams of H$_2$O |
| C. | 57.0 grams of choline chloride |

Component C was added to component B and A was then added to the whole. The whole composition was then mixed and the mixture was transferred to a polypropylene jar. Crystallization occurred under static conditions at 100° C. over 151 days. The crystalline product was separated, washed and dried and identified by X-ray diffraction analysis to be 100 percent new zeolite ZSM-45. The complete X-ray pattern data for this zeolite is presented in Table 4, hereinafter.

Chemical analysis of the zeolite product of this example proved it to have the following composition:

| Component | Wt. Percent |
|---|---|
| N | 2.26 |
| Na | 0.37 |
| K | 0.79 |
| Al$_2$O$_3$ | 7.48 |
| SiO$_2$ | 85.8 |
| Ash | 82.8 |
| SiO$_2$Al$_2$O$_3$,molar | 19.5 |

Sorption capacities of the zeolite product of this example, calcined at 538° C., were:

| Adsorbate | Capacity, Wt. Percent |
|---|---|
| Cyclohexane, 20 Torr | 3.4 |
| n-Hexane, 20 Torr | 12.9 |
| Water, 12 Torr | 21.1 |

The surface area of the zeolite product of this example was measured to be 471 m$^2$/gram.

TABLE 4

| Degrees Two Theta | Interplanar D-Spacing (A) | Relative Intensity, I/Io |
|---|---|---|
| 7.77 | 11.38 | 4 |
| 8.71 | 10.15 | 10 |
| 11.04 | 8.02 | 45 |
| 11.71 | 7.56 | 6 |
| 13.52 | 6.55 | 36 |
| 15.67 | 5.66 | 2 |
| 16.11 | 5.50 | 10 |
| 17.49 | 5.07 | 76 |
| 17.93 | 4.95 | 13 |
| 19.57 | 4.54 | 4 |
| 21.10 | 4.21 | 50 |
| 22.18 | 4.01 | 100 |
| 23.54 | 3.78 | 47 |
| 23.80 | 3.74 | 8 |
| 25.16 | 3.54 | 15 |
| 26.08 | 3.42 | 5 |
| 27.24 | 3.27 | 24 |
| 28.67 | 3.11 | 44 |
| 29.46 | 3.03 | 7 |
| 31.84 | 2.810 | 7 |
| 32.55 | 2.750 | 38 |
| 34.72 | 2.584 | 9 |
| 35.42 | 2.534 | 3 |
| 35.62 | 2.520 | 2 |
| 36.28 | 2.476 | 5 |
| 37.42 | 2.403 | 2 |
| 38.22 | 2.355 | 1 |
| 38.48 | 2.339 | 1 |
| 39.95 | 2.257 | 2 |
| 40.50 | 2.227 | 2 |
| 41.36 | 2.183 | 3 |
| 42.40 | 2.132 | 3 |
| 43.12 | 2.098 | 7 |
| 44.70 | 2.027 | 6 |
| 45.22 | 2.005 | 4 |
| 47.35 | 1.920 | 2 |
| 48.16 | 1.889 | 5 |
| 49.03 | 1.858 | 4 |
| 49.50 | 1.841 | 3 |
| 50.23 | 1.816 | 6 |
| 51.76 | 1.766 | 11 |

TABLE 4-continued

| Degrees Two Theta | Interplanar D-Spacing (A) | Relative Intensity, I/Io |
|---|---|---|
| 53.01 | 1.727 | 2 |
| 53.75 | 1.705 | 2 |
| 55.68 | 1.651 | 3 |
| 56.15 | 1.638 | 6 |
| 56.99 | 1.616 | 2 |
| 57.39 | 1.605 | 1 |
| 59.30 | 1.558 | 4 |

EXAMPLE 8

This Example demonstrates the preparation of ZSM-45 with a dimethyldiethylammonium directing agent. Sodium aluminate (29.8 percent $Na_2O$, 41.8 percent $Al_2O_3$), 0.5 g, was dissolved in 40.5 g of a 20 percent dimethyldiethylammonium hydroxide solution. A 50 percent sodium hydroxide solution, 0.5 g, and, finally, 8.3 g of Hi-Sil, a precipitated silica containing about 87 percent $SiO_2$, were added. The reaction mixture had the following composition:

| | |
|---|---|
| $SiO_2/Al_2O_3$ | = 60 |
| $(Na_2O + DMDEA_2O)/SiO_2$ | = 0.32 |
| $Na_2O/(Na_2O + DMDEA_2O)$ | = 0.14 |
| $H_2O/(Na_2O + DMDEA_2O)$ | = 48 |

The mixture was heated at 130° C. for 23 days. A sample of the product was dried at room temperature. This dried sample gave the X-ray diffraction pattern listed in Table 5.

TABLE 5

| Degrees Two Theta | Interplanar D-Spacing (A) | Relative Intensity, I/Io |
|---|---|---|
| 8.69 | 10.18 | 12 |
| 11.01 | 8.04 | 40 |
| 11.73 | 7.54 | 8 |
| 13.46 | 6.58 | 38 |
| 16.05 | 5.52 | 6 |
| 17.44 | 5.08 | 69 |
| 17.81 | 4.98 | 21 |
| 21.18 | 4.20 | 47 |
| 22.09 | 4.02 | 100 |
| 23.43 | 3.80 | 28 |
| 25.26 | 3.53 | 3 |
| 27.13 | 3.29 | 21 |
| 28.77 | 3.10 | 33 |
| 29.31 | 3.05 | 12 |
| 32.04 | 2.793 | 11 |
| 32.41 | 2.762 | 36 |
| 34.78 | 2.579 | 8 |
| 35.00 | 2.564 | 5 |
| 36.14 | 2.485 | 2 |
| 38.42 | 2.343 | 3 |
| 39.80 | 2.265 | 3 |
| 41.13 | 2.194 | 2 |
| 42.37 | 2.133 | 3 |
| 43.02 | 2.102 | 5 |
| 44.92 | 2.018 | 3 |
| 45.15 | 2.008 | 4 |
| 48.50 | 1.877 | 4 |
| 49.26 | 1.850 | 5 |
| 50.07 | 1.822 | 5 |
| 51.85 | 1.763 | 8 |
| 55.91 | 1.644 | 7 |
| 59.05 | 1.564 | 3 |

The product was calcined for 4 hours at 500° C. The calcined product gave the X-ray diffraction pattern listed in Table 6. It still contained an amorphous impurity and had the following sorption capacities, g/100 g.

| | |
|---|---|
| Cyclohexane, 20 Torr | 3.6 |
| n-Hexane, 20 Torr | 14.8 |
| Water, 12 Torr | 16.7 |

The chemical composition of the sample dried at room temperature was, wt. percent:

| | |
|---|---|
| $SiO_2$ | 70.0 |
| $Al_2O_3$ | 4.4 |
| $Na_2O$ | 0.73 |
| N | 2.30 |
| Ash | 76.9 |
| $SiO_2/Al_2O_3$, molar | 27.0 |

TABLE 6

| Degrees Two Theta | Interplanar D-Spacing (A) | Relative Intensity, I/Io |
|---|---|---|
| 8.73 | 10.13 | 18 |
| 11.05 | 8.01 | 85 |
| 11.73 | 7.54 | 12 |
| 13.55 | 6.54 | 100 |
| 16.15 | 5.49 | 4 |
| 17.53 | 5.06 | 35 |
| 17.90 | 4.96 | 10 |
| 21.12 | 4.21 | 41 |
| 22.19 | 4.01 | 84 |
| 23.60 | 3.77 | 25 |
| 25.36 | 3.51 | 7 |
| 26.10 | 3.41 | 7 |
| 27.27 | 3.27 | 22 |
| 28.72 | 3.11 | 35 |
| 29.46 | 3.03 | 9 |
| 31.90 | 2.805 | 8 |
| 32.58 | 2.749 | 41 |
| 34.78 | 2.579 | 8 |
| 35.03 | 2.562 | 3 |
| 36.33 | 2.473 | 3 |
| 38.49 | 2.339 | 1 |
| 40.01 | 2.254 | 2 |
| 41.36 | 2.183 | 3 |
| 42.39 | 2.132 | 2 |
| 43.21 | 2.094 | 4 |
| 44.75 | 2.025 | 2 |
| 45.15 | 2.008 | 2 |
| 48.22 | 1.887 | 2 |
| 49.18 | 1.853 | 4 |
| 50.36 | 1.812 | 2 |
| 51.91 | 1.761 | 8 |
| 56.10 | 1.639 | 5 |
| 59.45 | 1.555 | 3 |

It is noted that when dimethyldiethylammonium directing agents are used, sufficiently higher $SiO_2:Al_2O_3$ ratios than employed in this Example may lead to the production of ZSM-12 in addition to or instead of ZSM-45. Similarly, when a DMDEA directing agent is used, sufficiently lower $SiO_2:Al_2O_3$ ratios than employed in this Example may lead to the production of zeolite Y in addition to or instead of ZSM-45.

EXAMPLE 9

One gram of sodium aluminate (29.8 percent $Na_2O$, 41.8 percent $Al_2O_3$) was dissolved in 37.25 g of 20 percent aqueous dimethyldiethylammonium hydroxide solution. Hi-Sil (87 percent $SiO_2$), 8.3 g, was added and dispersed. The reaction mixture had the following composition:

| | |
|---|---|
| $SiO_2/Al_2O_3$ | 26.45 |
| $(Na_2O + DMDEA_2O)/SiO_2$ | 0.30 |
| $Na_2O/(Na_2O + DMDEA_2O)$ | 0.133 |

| -continued | |
|---|---|
| H₂O/(Na₂O + DMDEA₂O) | 49 |
| OH⁻/SiO₂ | 0.60 |

The mixture was heated at 160° C. in an autoclave at autogenous pressure.

A crystalline product was obtained after 21 days. It consisted mainly of ZSM-45, but contained a trace of an unidentified crystalline material. It had the following sorption capacities, g/100 g:

| Cyclohexane, 20 torr | 2.1 |
|---|---|
| n-Hexane, 20 torr | 13.5 |
| Water, 12 torr | 19.8 |

The chemical composition was, wt. percent:

| SiO₂ (by difference) | 71.1 |
|---|---|
| Al₂O₃ | 6.4 |
| Na₂O | 0.38 |
| N | 2.21 |
| Ash | 77.9 |
| SiO₂/Al₂O₃, molar | 18.9 |

EXAMPLE 10

This Example demonstrates the preparation of ZSM-45 with a cobalticinium directing agent. A cobalticinium ion is represented by the following formula:

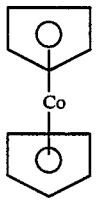

Crystallization was achieved utilizing a reaction mixture containing cobalticinium hexafluorophosphate, water, Q-brand sodium silicate, (27.8 percent SiO₂; 8.4 percent Na₂O; 63.8 percent H₂O), sodium hydroxide and Al₂(SO₄)₃.16H₂O. The mole ratio of H₂O:SiO₂ was 40. The crystallization was carried out at 160° C. while stirring at autogenous pressure. Reaction conditions and results are summarized in Table 7.

Analysis indicated that the product had a carbon to cobalt atomic ratio of 10.5, and a sodium oxide to silica to cobalt molar ratio per mole of Al₂O₃ wherein cobalt is expressed in terms of moles of CoO, of 1.13:13.6:0.90.

TABLE 7
Crystallization with Cobalticinium Ion
Mixture Composition (Mole Ratios)

| $\frac{SiO_2}{Al_2O_3}$ | $\frac{OH^-}{SiO_2}$ | $\frac{Na^+}{SiO_2}$ | $\frac{Co}{SiO_2}$ | Days | Product |
|---|---|---|---|---|---|
| 15 | 0.40 | 0.76 | 0.10 | 6 | ZSM-45 |

EXAMPLE 11

The procedure of Example 10 was followed except that the Na⁺:SiO₂ ratio was decreased from 0.76 to 0.53. Analysis indicated that the product had a carbon to cobalt atomic ratio of 10.8, and a sodium oxide to silica to cobalt molar ratio per mole of Al₂O₃, wherein cobalt is expressed in terms of moles of CoO, of 1.08:13.3:1.1. Reaction conditions and results are summarized in Table 8.

TABLE 8
Crystallization with Cobalticinium Ion
Mixture Composition (Mole Ratios)

| $\frac{SiO_2}{Al_2O_3}$ | $\frac{OH^-}{SiO_2}$ | $\frac{Na^+}{SiO_2}$ | $\frac{Co}{SiO_2}$ | Days | Product |
|---|---|---|---|---|---|
| 15 | 0.40 | 0.53 | 0.10 | 6 | ZSM-45 |

EXAMPLE 12

The procedure of Example 10 was followed except that the Na⁺:SiO₂ ratio was increased from 0.76 to 0.93 and crystallization time was decreased from 6 days to 2 days. A partial crystallization of ZSM-45 was achieved. Reaction conditions and results are summarized in Table 9.

TABLE 9
Crystallization with Cobalticinium Ion
Mixture Composition (Mole Ratios)

| $\frac{SiO_2}{Al_2O_3}$ | $\frac{OH^-}{SiO_2}$ | $\frac{Na^+}{SiO_2}$ | $\frac{Co}{SiO_2}$ | Days | Product |
|---|---|---|---|---|---|
| 15 | 0.40 | 0.93 | 0.10 | 2 | Part. crystn. ZSM-45 |

COMPARATIVE EXAMPLE C

This Comparative Example again demonstrates that ZSM-45 will not form unless sufficient ZSM-45 forming conditions are maintained. More particularly, the procedure of Example 10 was followed except that the SiO₂:Al₂O₃ ratio was increased from 15 to 30, the Na+:SiO₂ ratio was increased from 0.76 to 0.91 and the crystallization time was decreased from 6 days to 2 days. It is noted that the procedure of this Comparative Example corresponds very closely to the procedure of Example 12 except that the SiO₂:Al₂O₃ ratio is increased from 15 to 30 and the Na+:SiO₂ ratio was decreased from 0.93 to 0.91. Reaction conditions and results are summarized in Table 10.

TABLE 10
Crystallization with Cobalticinium Ion
Mixture Composition (Mole Ratios)

| $\frac{SiO_2}{Al_2O_3}$ | $\frac{OH^-}{SiO_2}$ | $\frac{Na^+}{SiO_2}$ | $\frac{Co}{SiO_2}$ | Days | Product |
|---|---|---|---|---|---|
| 30 | 0.40 | 0.91 | 0.10 | 2 | not ZSM-45 |

As indicated by Table 10, the product of the crystallization of this Comparative Example is not ZSM-45. The formation of a zeolite other than ZSM-45 according to this Comparative Example is believed to be primarily attributable to the use of the relatively high ratio of SiO2:Al₂O₃.

COMPARATIVE EXAMPLE D

This Comparative Example further demonstrates that ZSM-45 will not form unless sufficient ZSM-45 forming conditions are maintained. More particularly, crystallization was again carried out at 160° C. while stirring at autogenous pressure but the reaction mixture contained potassium silicate manufactured by the Philadelphia Quartz Company under their tradename "KASIL-88", $Al_2(SO_4)_3.16\ H_2O$, water, and the cobalticinium hexafluorophosphate. The mole ratio of $H_2O:SiO_2$ was 40. The zeolite of Comparative Example C formed instead of ZSM-45. Reaction conditions and results are summarized in Table 11.

TABLE 11

| Crystallization with Cobalticinium Ion | | | | | |
|---|---|---|---|---|---|
| Mixture Composition (Mole Ratios) | | | | | |
| $\frac{SiO_2}{Al_2O_3}$ | $\frac{OH^-}{SiO_2}$ | $\frac{K^+}{SiO_2}$ | $\frac{Co}{SiO_2}$ | Days | Product |
| 60 | 0.40 | 0.61 | 0.10 | 3 | not ZSM-45 | is expressed in terms of moles of CoO, of 0.70:8.6:0.61.

TABLE 13

| Crystallization with Cobalticinium Ion | | | | | |
|---|---|---|---|---|---|
| Mixture Composition (Mole Ratios) | | | | | |
| $\frac{SiO_2}{Al_2O_3}$ | $\frac{OH^-}{SiO_2}$ | $\frac{Na^+}{SiO_2}$ | $\frac{Co}{SiO_2}$ | Days | Product |
| 60 | 0.40 | 0.61 | 0.10 | 3 | ZSM-45 + Contaminant |

The results of all the crystallizations with a cobalticinium directing agent as reported herein in Tables 7-13 are summarized in Table 14.

TABLE 14

| | Crystallization with Cobalticinium Ion | | | | | | |
|---|---|---|---|---|---|---|---|
| | Mixture Composition (Mole Ratios) | | | | | | |
| Table | $\frac{SiO_2}{Al_2O_3}$ | $\frac{OH^-}{SiO_2}$ | $\frac{Na^+}{SiO_2}$ | $\frac{K^+}{SiO_2}$ | $\frac{Co}{SiO_2}$ | Days | Product |
| 7[b] | 15 | 0.40 | 0.76 | — | 0.10 | 6 | ZSM-45 |
| 8[b] | 15 | 0.40 | 0.53 | — | 0.10 | 6 | ZSM-45 |
| 9[b] | 15 | 0.40 | 0.93 | — | 0.10 | 2 | Part. crystn. ZSM-45 |
| 10[b] | 30 | 0.40 | 0.91 | — | 0.10 | 2 | not ZSM-45 |
| 11[c] | 60 | 0.40 | — | 0.61 | 0.10 | 3 | not ZSM-45 |
| 12[d] | 30 | 0.55 | 0.67 | — | 0.10 | 6 | ZSM-45 |
| 13[b] | 30 | 0.45 | 0.57 | — | 0.10 | 6 | ZSM-45 + Comtaminant |

[a] $\frac{H_2O}{SiO_2} = 40$

[b] Silica sol (30 percent $SiO_2$); Na $AlO_2$; NaOH
[c] Kasil-88 potassium silicate; $Al_2(SO_4)_3.16\ H_2O$
[d] Q-brand sodium silicate; $Al_2(SO_4)_3.16\ H_2O$; NaOH

EXAMPLE 13

The procedure of Examples 10-12 was followed with the exception that silica sol (30 percent $SiO_2$) and sodium aluminate were substituted for the Q-brand sodium silicate and the aluminum sulfate. Analysis indicated that the product had a carbon to cobalt atomic ratio of 10.6, and a silica to cobalt molar ratio per mole of $Al_2O_3$, wherein cobalt is expressed in terms of moles of CoO, of 8.7:0.55. Reaction conditions and results are summarized in Table 12.

TABLE 12

| Crystallization with Cobalticinium Ion | | | | | |
|---|---|---|---|---|---|
| Mixture Composition (Mole Ratios) | | | | | |
| $\frac{SiO_2}{Al_2O_3}$ | $\frac{OH^-}{SiO_2}$ | $\frac{Na^+}{SiO_2}$ | $\frac{Co}{SiO_2}$ | Days | Product |
| 10 | 0.55 | 0.67 | 0.10 | 6 | ZSM-45 |

EXAMPLE 14

The procedure of Example 13 was followed except that the $OH^-:SiO_2$ ratio was decreased from 0.55 to 0.45 and the $Na^+:SiO_2$ ratio was decreased from 0.67 to 0.57. The product was ZSM-45 plus an unidentified contaminant. Reaction conditions and results are summarized in Table 13.

Analysis indicated that the product had a carbon to cobalt atomic ratio of 10.7, and a sodium oxide to silica to cobalt molar ratio per mole of $Al_2O_3$, wherein cobalt

EXAMPLE 15

A ZSM-45 sample, prepared in the general manner described in Examples 1 and 2, is used in its ammonium exchanged form to convert methanol to hydrocarbons in known manner. The ZSM-45 used in such conversion has a silica/alumina ratio of about 26 and the following sorption capacity and alkali metal content:

| | |
|---|---|
| Cyclohexane, wt. %: | 3.5 |
| n-Hexane, wt. %: | 11.2 |
| $H_2O$, wt. %: | 18.0 |
| Residual Na, wt. %: | 0.28 |
| Residual K, wt. %: | 0.1 |

In such a procedure, 2 grams of zeolite (no binder) and 4 grams of quartz chips, both of 14/20 mesh size, are mixed and packed into a stainless steel microreactor, equipped with thermocouple. Methanol is fed to the reactor under hydrogen pressure under varying reaction conditions for a period of up to 177 hours. Pressure during the run is maintained at 125 psi. A WHSV for methanol of 0.4 is used. Data points are taken at various times during the run. The total reactor effluent is analyzed, on line, by gas chromatography. Methanol conversion is calculated based on hydrocarbon formation only. Selectivities (wt. %) to hydrocarbon product are calculated on "coke free" basis. A catalyst aging rate defined as the amount of change in percent methanol conversion to hydrocarbon per hour is also computed. Reaction conditions, as well as methanol conversion results for this run, are set forth in Table 15.

TABLE 15

| | Methanol Conversion to Light Olefins Over Zeolite ZSM-45 | | | | | | |
|---|---|---|---|---|---|---|---|
| Run No. | 1 | 2 | 3 | 4 | 5 | 6 | 7 |
| Time on Stream, hours | 1–22 | 22–29 | 29–49 | 49–55 | 55–70 | 70–95 | 95–177 |
| Temperature, °C. | 350–372 | 391 | 400 | 400 | 402 | 402 | 402 |
| $H_2$/MeOH molar ratio | 10 | 10 | 10 | 4 | 4 | 1.5 | 1 |
| Percent Conversion | 22 | 76 | 96 | 95 | 98 | 82 | 61 |
| Product Selectivity (wt. %) | | | | | | | |
| $C_2H_4$ | 35.8 | 58.2 | 57.2 | 54.8 | 49.9 | 51.4 | 46.2 |
| $C_3H_6$ | 21.8 | 16.1 | 15.2 | 21.0 | 23.0 | 28.0 | 28.7 |
| $C_2H_4$—$C_4H_8$ | 64.6 | 75.4 | 73.2 | 77.3 | 75.0 | 81.8 | 78.2 |
| $CH_4$—$C_3H_8$ | 29.4 | 23.8 | 26.3 | 22.3 | 24.3 | 17.4 | 20.3 |
| Aging Rate, Percent Per Hour | — | 0 | 0 | 0.34 | 0 | 0.63 | 0.24 |

The Table 15 data indicate that for a molar ratio of $H_2$/MeOH of 10 and at 400° C., methanol conversion results of about 95% can be achieved. Selectivities to ethylene and total light olefins are greater than 55% and 75%, respectively, under these conditions. When the molar ratio of $H_2$/MeOH was lowered to 1 (Run No. 7), the catalyst maintains its activity and selectivities for more than 80 hours. During this period, the ethylene selectivity ranges from 40–50%. Total light olefin selectivity is greater than 75%. The aging rate for methanol conversion under this condition is only 0.24% per hour. Such results clearly show the effectiveness of Zeolite ZSM-45 under hydrogen pressure in promoting the selective conversion of methanol to a hydrocarbon product enriched in light olefins.

COMPARATIVE EXAMPLE E

This Comparative Example demonstrates the comparatively rapid aging of the ZSM-45 catalyst in the production of olefins from methanol when a hydrogen-containing gas is omitted from the chargestock. Two grams $NH_4$ ZSM-45 pelletized to 14/20 mesh and diluted with 4 gram quartz chips, was packed into a quartz microreactor. The catalyst was calcined at 500° C. for at least 16 hours with air. The catalyst bed temperature was then lowered to 300° C. under $N_2$ atmosphere. Methanol (37.2% by weight) diluted with water was then fed through the catalyst bed at atmospheric pressure. The WHSV of methanol was 0.7 and WHSV of $H_2O$ was 1.2. The total reactor effluent was analyzed by g.c. equipped with an N-octane on poracil column. Methanol conversion was calculated based on conversion to hydrocarbons only. The reaction results were summarized in Table 1. As Run #1 to 7 demonstrated, the catalyst activity for methanol conversion to hydrocarbons decreased to 32.7% after eight hours on stream using water as diluent. After regeneration with air, methanol conversion decreased to 6.5% after three hours on stream using $H_2O$ as diluent (Run #8 to 11).

What is claimed is:

1. A process for converting a feedstock comprising methanol, methyl ether or mixtures thereof to product comprising olefins, which comprises co-feeding said feedstock along with a gaseous diluent comprising a hydrogen-containing gas into a reaction zone maintained under conversion conditions with a catalyst comprising a synthetic porous crystalline aluminosilicate zeolite material capable of sorbing cyclohexane and having a silica to alumina ratio of at least 8, said porous crystalline material being characterized by an X-ray diffraction pattern exhibiting values substantially as set forth in Table 1 of the specification, wherein said conversion conditions comprise a pressure of at least $3 \times 10^5$ $N/m^2$.

2. The process of claim 1, wherein said zeolite has a composition on an anhydrous basis and in terms of moles of oxides per mole of alumina, expressed by the formula:

$$(1-2.6) \, M_{2/m} \, O : Al_2O_3 : xSiO_2 \qquad (I)$$

wherein M represents one or more cations having valence m and x is at least 8, provided that if M represents hydrogen, each hydrogen atom is bound to an anionic site on teterahedra of said zeolite containing aluminum atoms.

3. The process of claim 1, wherein said zeolite in as synthesized form has a composition, on an anhydrous basis and in terms of moles of oxides per mole of alumina, expressed by the formula:

$$(0.5-1.8)R_2O : (0.0-0.3)Na_2O : (0.0-0.5)K_2O : Al_2O_3 : xSiO_2$$

wherein $R_2O$ is the oxide form of a suitable directing agent and x is at least 8.

4. The process of claim 3 wherein x is from greater than 8 to about 100.

TABLE 16

| | Methanol Conversion and Product Selectivity as a function of time on stream by ZSM-45 catalyst, using water as diluent. | | | | | | | | | | |
|---|---|---|---|---|---|---|---|---|---|---|---|
| Run No. | 1 | 2 | 3 | 4 | 5 | 6 | 7 | 8 | 9 | 10 | 11 |
| Time on Stream (hrs.) | 1.0 | 1.7 | 2.5 | 4.0 | 4.6 | 6.0 | 8.0 | 0.5 | 1.3 | 2.0 | 3.3 |
| MeOH Conversion ($CH_2$ %) | 16 | 100 | 100 | 100 | 92 | 62.8 | 32.7 | 26.3 | 87.4 | 37.3 | 6.5 |
| Product Selectivity (wt. %) | | | | | | | | | | | |
| $C_2C_4$ | 52.2 | 31.8 | 36.4 | 23.5 | 43.7 | 40.9 | 44.1 | 45.4 | 40.7 | 35.6 | 34.9 |
| $C_3H_6$ | 5.8 | 11.4 | 26.3 | 25.6 | 28.0 | 32.1 | 34.5 | 12.4 | 27.5 | 27.8 | 33.8 |
| $CH_4$—$C_3H_8$ | 37.8 | 38.6 | 22.2 | 32.6 | 20.8 | 21.2 | 13.5 | 34.2 | 23.9 | 29.4 | 25.6 |
| $C_2H_4$—$C_4H_8$ | 59.1 | 48.6 | 69.4 | 56.6 | 75.7 | 76.8 | 84.4 | 59.7 | 72.8 | 66.8 | 73.2 |
| Others | 3.1 | 12.8 | 8.4 | 10.8 | 3.5 | 2.0 | 2.1 | 6.1 | 3.3 | 3.8 | 1.2 |

5. The process of claim 3 wherein R is a cation selected from the group consisting of 2-(hydroxyalkyl) trialkylammonium and dimethyldiethylammonium.

6. The process of claim 3 wherein R is an organic cation derived from 2-(hydroxyalkyl) trialkylammonium chloride.

7. The process of claim 3 wherein said catalyst comprises the product of thermal treatment of the as synthesized form of said zeolite.

8. The process of claim 1 wherein said catalyst comprises said crystalline material having original cations replaced, at least in part, with a cation or a mixture of cations selected from the group consisting of hydrogen and hydrogen precursors, rare earth metals, and metals of Groups IA, IIA, IIIA, IVA, IB, IIB, IIIB, IVB, VIB and VIII of the Periodic Table of the Elements.

9. The process of claim 7 wherein said product of thermal treatment of said crystalline material has had original cations replaced, at least in part, with a cation or a mixture of cations selected from the group consisting of hydrogen and hydrogen precursors, rare earth metals, and metals of Groups IA, IIA, IIIA, IVA, IB, IIB, IIIB, IVB, VIB and VIII of the Periodic Table of the Elements.

10. The process of claim 8 wherein said crystalline material having original cations replaced, at least in part, has been thermally treated.

11. The process of claim 1 wherein said conversion reaction conditions include a reaction temperature of from about 300° C. to 450° C. and a pressure of from about $3 \times 10^5 N/m^2$ to $1.5 \times 10^6 N/m^2$.

12. The process of claim 1 wherein said conversion reaction conditions include a weight hourly space velocity for the organic reactants of from about 0.1 to 30.

13. The process of claim 1 wherein said organic reactant feed consists essentially of anhydrous methanol.

14. The process of claim 1 wherein said organic reactant feed consists essentially of methanol-water mixtures.

15. The process of claim 1 wherein said organic reactant feed consists essentially of methanol-methyl ether mixtures.

16. A process for converting an organic reactant feed comprising methanol, methyl ether and mixtures thereof to an olefin-containing hydrocarbon product, said process comprising co-feeding said organic reactant feed along with substantially pure hydrogen into a reaction zone under conversion reaction conditions including a temperature between about 260° C. and 540° C., a pressure between about $3 \times 10^5 N/m^2$ and $1.5 \times 10^6 N/m^2$, a weight hourly space velocity for the organic reactants of between about 0.01 and 30 and a weight hourly space velocity for hydrogen of from about 0.003 to 20, with a zeolite-based catalyst composition comprising a synthetic porous crystalline aluminosilicate zeolite material capable of sorbing cyclohexane and having a silica to alumina ratio of at least 8, said porous crystalline material being characterized by an X-ay diffraction pattern exhibiting values substantially as set forth in Table 1 of the specification, to thereby form a $C_2$–$C_4$ olefin-containing reaction product.

* * * * *

UNITED STATES PATENT AND TRADEMARK OFFICE
CERTIFICATE OF CORRECTION

PATENT NO. : 4,912,281

DATED : March 27, 1990

INVENTOR(S) : Margaret M. Wu

It is certified that error appears in the above-identified patent and that said Letters Patent is hereby corrected as shown below:

Col. 4, line 49; "a" should be --as--

Col. 5, line 66; "adsorbent" should be --adsorbate--

Col. 9, line 8; "xontmorillonite" should be --montmorillonite--

Col. 15, line 9; delete "c.190.0 grams of choline chloride" (extra line)

Col. 24, Table 14; under the 1st column headed "Table", "13$^b$" should be --13$^d$--

Col. 24, Table 14; under the 2nd column headed "$\frac{SiO_2}{Al_2O_3}$", the last 2 entries "30" and "30" should be --10-- and --10--

Col. 26, line 19; delete "a gaseous diluent comprising"

Col. 28, line 28; "X-ay" should be --X-ray--

Signed and Sealed this

Twenty-seventh Day of August, 1991

Attest:

HARRY F. MANBECK, JR.

Attesting Officer

Commissioner of Patents and Trademarks